United States Patent [19]
Jones et al.

[11] Patent Number: 6,051,393
[45] Date of Patent: Apr. 18, 2000

[54] METHOD OF DETECTING MALIGNANT AND PRE-MALIGNANT CONDITIONS OF THE CERVIX, AND TEST KITS THEREFOR

[76] Inventors: Sonja K. Jones, 25B Butler Road, Harrow, Middlesex HA1 4DS; Trevor F. Slater, deceased, late of Stanmore; by Hazel Slater, administrator, Stanburn House, 69 Old Church Lane, Stanmore, Middlesex HA7 2RG, all of United Kingdom

[21] Appl. No.: 08/314,923

[22] Filed: Sep. 29, 1994

Related U.S. Application Data

[63] Continuation of application No. 08/219,771, Mar. 29, 1994, abandoned.

[51] Int. Cl.⁷ .............................. C12Q 1/02; G01N 33/48
[52] U.S. Cl. .................................... 435/29; 435/3; 435/4; 435/810; 436/64; 436/808; 436/813; 424/9.1
[58] Field of Search ............................ 435/29, 3, 4, 810; 436/64, 808, 813; 424/9.1

[56] References Cited

U.S. PATENT DOCUMENTS

| | | | |
|---|---|---|---|
| 3,857,033 | 12/1974 | Cobb | 250/303 |
| 4,317,877 | 3/1982 | Balis et al. | 435/7.1 |

FOREIGN PATENT DOCUMENTS

| | | |
|---|---|---|
| 0 042 482 | 12/1981 | European Pat. Off. . |
| 1303881 | 4/1987 | U.S.S.R. . |
| 1318568 | 5/1973 | United Kingdom . |
| 2 198 846 | 6/1988 | United Kingdom . |

OTHER PUBLICATIONS

Cohen et al, *Br. Med. J.*, vol. 1, pp. 88–89, 1966.
Shield et al., The Australian and New Zealand Journal of Obstetrics & Gynecology, vol. 27, No. 4, pp. 266–282, 1987.
Rounds et al, *Gynecologic Oncology*, vol. 4, No. 2, pp. 125–132, 1976.
Wiernik et al, *Br. J. Cancer*, vol. 28, No. 6, pp. 488–499, 1973.
Cohen et al, *Br. Med. J.*, vol. 1, pp. 88–89, 1966.
Nilson et al, *Arch. Gynecol.*, vol. 240, pp. 75–79, 1987.
Cohen et al, *Br. Med. J.*, vol. 1, pp. 88–89, 1966.
Shield et al, *The Australian and New Zealand Journal of Obstetrics & Gynecology*, vol. 27, No. 4, pp. 269–282, 1987.
Jonas et al, *Br. J. Cancer*, vol. 66, pp. 185–189, 1992.
Moncrieff et al, *Anal. Quant. Cytol.*, vol. 6, No. 3, pp. 201–205, Sep. 1984.
Wiernik et al, *Br. J. Cancer*, vol. 28, No. 6, pp. 488–499, Dec. 1973.
Rounds et al, *Gynecologic Oncology*, vol. 4, No. 2, pp. 125–132, Jun. 1976.
Wiernik et al, Abstract from EMBASE No. 7416790 (Search Report) [Brit. J. Cancer, (1973) 28/6 (488–499].
Bendetto et al., 1990, "Quantitative measurements of the changes in protein thiols in cervical intraepithelial neoplasia and in carcinoma of the human uterine cervix provide evidence for the existence of a biochemical field effect", Cancer Res. 50:6663–67.

Buchan et al., 1969, "Immunological specificity of thymidine kinases in cells infected by viruses of the herpes group", J. Gen. Virol. 4 (pt. 3):461–63.
Chayen et al., 1986, "Cellular biochemistry of glucose–6–phosphate and 6–phosphogluconate dehydrogenase activities", Cell Biochem. Function 4:249–53.
Chayen et al., 1962, "Histochemical demonstration of 6–phosphogluconate dehydrogenase in proliferating and malignant cells", Nature 195:714–15.
Cohen and Way, 1966, "Histochemical demonstration of pentose shunt activity in smears form the uterine cervix", Br. Med. J. 1:88–89.
Coulton, 1977, "Temporal relationship between glucose–6–phosphate dehydrogenase activity and DNA–synthesis", Histochemistry 50:207–15.
Glock and McLean, 1954, "Levels of enzymes of the direct oxidative pathway of carbohydrate metabolism in mammalian tissues and tumors", Bichemistry J. 56:171–75.
Ismail et al., 1989, "Observer variation in histopathological diagnosis and grading of cervical intraepithelial neoplasia", BMJ 298:707–10.
Ives et al., 1969, "Rapid determination of nucleoside kinase and nucleosidase activities with tritium–labeled substrates", Analytical Biochemistry 28:192–205.
Johnson and Rowlands, 1989, "Diagnosis and treatment of cervical intraepithelial neoplasia in general practice," BMJ 299:1083–86.
Mitchell and Medley, 1991, "Longitudinalstudy of women with negative cervical smears according to endocervical status", The Lancet 337:265–67.
Mitchell et al., 1990, "Cervical cancers diagnosed after negative results on cervical cytology: perspective in the 1980s", Br. Med. J. 300:1622–26.
McDermott et al., 1990, "Premorphological metabolic changes in human breast carcinogenesis", Br. J. Surg. 77:1179–82.
McIndoe et al., 1984, "The invasive potential of carcinaoma in situ of the cervix," Ostetrics & Gynecology 64:451–58.
Nilson et al., 1987, "Histochemical investigation of cervical intraepithelial neoplasia", Arch. Gynecol. 240:75–79.
vanNooren and Tas, 1980, "Quantitative aspects of the cytochemical demonstration of glucose–6–phosphate dehydrogenase with tetranitro BT studied in a model system of polyacrylamide films", Histochemical J. 12:669–85.
Salser et al., 1976, "Foetal thymidine kinase in tumours and colonic flat mucosa of man", Nature 260:261–63.
Salser et al., 1973, "Distribution and regulation of deoxythymidine kinase activity in differentiating cells of mammalian intestines", Cancer Res. 33:1889–97.

(List continued on next page.)

*Primary Examiner*—Cecilia J. Tsang
*Assistant Examiner*—Abdel A. Mohamed
*Attorney, Agent, or Firm*—Nixon & Vanderhye P.C.

[57] ABSTRACT

A method of detecting malignant or pre-malignant conditions of the cervix, and test kits therefor, involves selecting a fraction of a cervical cell sample consisting predominantly of epithelial cells and determining characteristics indicative of the malignant or pre-malignant conditions therein.

42 Claims, No Drawings

OTHER PUBLICATIONS

Scott et al., 1982, "Retinoids increase transglutaminase activity and inhibit ornithine decarboxylase activity in Chinese ovary hamster cells and in melanoma cells stimulated to differentiate", Proc. Natl. Acad. Sci. USA 79:4093–97.

Shield et al., 1987, "The pap smear revisited", Aust. NZ J. Obstet. Gynaecol. 27:269–82.

Slater et al., 1985, "Protein thiols in normal and neoplastic human uterine cervix", FEBS Letts. 187:267–71.

Slater and Sawyer, 1962, "A colorimetric method for estimating the pyridine nucleotide content of small amounts of animal tissue", Nature 193:454–456.

Wheelock and Kaminski, 1989, "Value of repeat cytology at the time of colposcopy for the evaluation of cervical intraepithelial neoplasia on papanicolaou smears", J. Reprod. Med. 34:815–17.

Weber, 1977, "Enzymology of cancer cells", N. Engl. J. Med. 296:486–51.-

METHOD OF DETECTING MALIGNANT AND PRE-MALIGNANT CONDITIONS OF THE CERVIX, AND TEST KITS THEREFOR

This application is a continuation of Ser. No.: 08/219,771 Filed: Mar. 29, 1994, now abandoned.

This invention relates to the detection of malignant and pre-malignant conditions of the uterine cervix and more particularly to test procedures based on examination of cell samples derived by cervical smear.

Cancer of the cervix is a world-wide problem and in some countries a major cause of death by cancer in women. In its early and pre-malignant condition, known as cervical intra-epithelial neoplasia (CIN grades 1 to 3), the treatment of the disease is safe and successful. This emphasizes the importance of early and accurate diagnosis.

The standard procedure for detection of abnormal cells, malignant or pre-malignant, is the Papanicolaou test, commonly known as the Pap-test. It was introduced in the 1940s and has to date never been subjected to any major clinical trial to test its accuracy and reliability as an indicator of early lesions of the uterine cervix. However, epidemiological evidence suggests strongly that there are disturbingly high error rates associated with this test (Mitchell & Medley, Br Med J. 337, 265–267).The methodology consists of taking samples of material from the uterine cervix and smearing this onto a glass microscope slide followed by a staining procedure. The major criticisms are that the method relies on optimum sampling and experienced but subjective diagnosis by the cytologist. The test involves tedious microscopic examination carried out for long periods which introduce boredom and consequential errors. Above all, the method is not quantitative. Alternative approaches have been devised which include measurements based on DNA staining and estimation of degrees of aneupolidy but many of these methods are time-consuming and depend on sophisticated instrumentation for diagnosis, thus presenting an obstacle to automation.

It is an object of the present invention to provide a test for the medical conditions specified above which is more accurate and reliable than the existing Pap-test.

It is a further object of this invention to provide a test of the foregoing kind which enables a quantitative estimate to be made of the condition of the patient under test.

It is a still further object of this invention to provide a test of the foregoing kind which is amenable to automated procedures.

The present invention comprises a method of testing for a malignant or pre-malignant condition of the cervix by examination of a cervical cell sample, in which the test is performed on a fraction of the sample consisting predominantly of epithelial cells. The cervical cell sample from which the desired fraction of cells is to be examined is preferably obtained by cervical smear as in the conventional PAP test.

Various methods are available for selecting the epithelial fraction of the cells present in the original sample for the purposes of examination and test. Selection may involve physical removal of the desired fraction from unwanted cellular material but alternative methods are possible in which selection occurs, in effect, as part of the test procedure itself. Use may be made, for example, of methods of flow cytometry in procedures in which a discrete step of separating the epithelial cells may not be necessary. Flow cytometry may be used to separate cells according to size for sequent testing. Thus, a selective reaction of the epithelial cells, or substances present therein, with an antibody or other reagent may enable these cells to be identified and examined without the need for a prior step of physical removal of contaminant material. For example cells obtained from routine smears can be diluted in saline e.g PBS and thoroughly syringed to achieve single cell suspension. This can be fixed and stained using various fluorescent antibodies which may or may not bind to different cell types. Following washing the cell suspension can be subjected to flow cytometry. By raising a fluorescent antibody to a significant cell component e.g. an enzyme the cell type can be selected for by flow cytometry. If another fluorescent antibody is raised against another component it would be possible to measure the two antibodies simultaneously in the same population of cells.

Preferably, the desired fraction of cells is separated from other material by a discrete step which precedes the testing of the cells by methods to be described more fully hereinafter. Buoyant density methods are highly suitable for separating epithelial cells for the purposes of the invention. A particularly effective method is by density gradient centrifugation. Methods of this kind are highly effective for the removal of material such as inflammatory cells, cell debris and mucus which interfere with the assessment of the abnormalities under investigation.

Discontinuous gradient centrifugation methods are highly effective in obtaining sharp bands of the various fractions whereas continuous gradient methods are less useful and are not recommended. A wide range of gradient materials is available and suitable materials may be readily selected for use according to this invention depending on their osmolarities at the concentrations required, which must not be damaging to the cells, especially the epithelial cells. The common inorganic salt gradients eg caesium chloride are less preferred to the organic materials including glycerol, sucrose, dextran, bovine serum albumin, and the proprietary materials known as Percoll (colloidal silica product of Pharmacia) and Ficoll (a copolymer of sucrose and epichlorhydrin supplied by Pharmacia), Metrizamide and Nycodenz (iodinated aromatic compound products of Nyegaard). Percoll and Ficoll give excellent results for our purposes and are highly preferred.

It has been found that the desired band of cells to be separated is, or corresponds to, the fraction of density range from about 1.035 to about 1.055 grams per milliliter (g/ml) as measured in a Percoll density gradient. Methods other than density gradient techniques can alternatively be used to separate a fraction correlating with that in the specified Percoll density range.

After separation of the desired fraction a variety of methods of examining the cells may be utilised. Thus, the proportion of cells in the separated fraction which have abnormal characteristics can be determined by cell-counting. However, it will be understood that an important objective of the present invention is to provide a quantitative estimate of the stage to which the disease may have progressed. Quantitative methods for use according to the present invention fall into two main categories. The first of these includes tests carried out on intact cells which, for convenience of description, will be referred to herein as cytochemical methods. These methods usually involve the estimation of a marker substance formed in or taken up by the whole cells as, for example, when typical cell staining techniques are used. Cytochemical methods may make use of biochemical reactions carried out in the intact cells which result in the formation of a product which can be measured by spectrophotometric or colorimetric techniques or by other means, for example, using microdensitometry and flow cytometry.

The second category of quantitative methods for use in accordance with this invention includes tests carried out on lysed cells and cell extracts. These methods, which will be referred to as biochemical methods, are highly preferred. Biochemical methods entail the monitoring of the biochemistry of epithelial cells in order to detect differences between normal and abnormal cells. Of especial value in this connection are methods for determining the content of certain enzymes or other proteins, the expression of which may be raised above normal values in conditions of cell proliferation i.e. raised in activity or in amount, or both. For this purpose, use may be made of biochemical or immunoassay methods, including fluorescent monoclonal or polyclonal antibody binding of enzymes or other proteins. Suitable examples of such enzymes are the pentose phosphate shunt enzymes, ornithine decarboxylase (ODC), thymidine kinase (TK), and ribonucleotide reductase (RNR). At present the standard methods for the assay of both ODC and TK require the use of radioactive materials. They are described by Scott et al (1982) PNAS (USA), 79 4093 for ODC and Ives et al (1969) Anal. Biochem. 28 192 for TK. The use of non-radioactive materials in alternative methods eg calorimetric or fluorimetric methods or by antibody raising would be much preferred. At present the preferred choice is one or more of the pentose phosphate shunt enzymes, especially glucose-6-phosphate dehydrogenase and/or 6-phosphogluconate dehydrogenase. In order to carry out such dehydrogenase assays the cells may be lysed in detergent and the extract used for the assay, for example employing substrates consisting of NADP+ and glucose-6-phosphate or 6-phosphogluconate. The oxidations may be coupled to a cycling electron acceptor eg phenazine methosulphate (PHs) and a final electron acceptor eg dichlorophencindophenol (DcPIP) or nitroblue tetrazolium (NBT). Determination of activity may thus be achieved by spectrophotometry at 600 nm or microdensitometry at 540 nm.

Enzymatic assays of the foregoing kind may be readily carried out with the use of reagents supplied in the form of a kit in which the reagents are contained in separate containers in the customary way for biochemical assay kits. Each reagent may be separately packaged as a unit amount required for a single test or as multiple units from which aliquot amounts are dispensed when carrying out a series of such tests. For the above-mentioned reagents the substrate concentrations that are preferably used in order to avoid any reaction in the absence of these lie within 2.5 and 3.5 mM glucose-6-phosphate or 6-phosphogluconate; 0.45 and 0.55 mM NADP+; 0.055 and 0.065 mM DcPIP or NBT; 0.10 and 0.18 mM PMS for both the cytochemical and biochemical assay.

For the convenience of the operator, in addition to the assay reagents the kits preferably contain the gradient materials required for the preliminary centrifugal separation of the epithelial cells. These are supplied in the form of solutions or as dry materials for reconstitution at the desired concentrations over the density range necessary for the discontinuous gradient method eg as described above for Percoll.

It will therefore be appreciated that this invention provides a simple and reliable test of pre-malignancy which is based on (i) the separation of epithelial cells from the uterine cervix from contaminating material which may interfere with the test, and (ii) the development of sensitive methods for detection of abnormalities in these separated cells.

Also in accordance with this invention the sensitivity of the biochemical method can be amplified by means of an enzyme ratio measurement. Thus the assays of those enzymes mentioned above can be supplemented by measurement of the levels of activity of other enzymes which are repressed in malignant or pre-malignant cells. By the term "repressed" is meant present at a reduced level either in activity or in amount. The ratio of the two sets of enzymes (increased to decreased) gives a sensitive index of cellular abnormality. Examples of such repressed enzymes are catalase and xanthine oxidase which may be conveniently determined by known methods eg for catalase the production of oxygen in the presence of hydrogen peroxide.

Applying the biochemical methods described above, the enzymes of the pentose phosphate shunt have been measured, using an amplifying recycling technique by spectrophotometry and catalase was estimated either by the reduction in $H_2O_2$ concentration or by oxygen generation in an oxygen electrode system.

Practical Examples of the cell separation procedure and the reaction systems studied to produce the activity ratios used for diagnostic purposes as described below.

EXAMPLE 1

SAMPLING AND GRADIENT SEPARATION

Sampling

Cervical material is obtained from well-woman's clinics from patients undergoing routine check-ups and from colposcopy clinics from patients who have been referred due to suspected abnormality. The samples are collected using either a wooden spatula, a Jordan's spatula or various types of cytobrushes, and placed immediately into universal bottles containing sterile cold phosphate-buffered saline. Processing of these samples can be delayed up to 6 hours but is preferably carried out immediately after collection although it is possible to partially process the samples and then freeze them in 5–10% DMSO and carry out any appropriate assay several days later with only a small loss of enzyme activity.

In order to demonstrate that loss of enzyme activity is minimised various storage conditions have been tested on a mammalian epithelial cell line. The results for G6PD activity are given in Table 1.

TABLE 1

| storage conditions | time of assay days after processing | G6PD activity (units/min/$10^5$ cells) |
|---|---|---|
| none | immediately (control) | 0.100 |
| −70° C. | 4 | 0 |
| −70° C. (+1% DMSO) | 4 | 0.190 |
| −70° C. (+10% DMSO) | 4 | 0.070 |
| $N_2$ | 4 | 0.004 |
| $N_2$ (+1% DMSO) | 4 | 0.021 |
| $N_2$ (+10% DMSO) | 4 | 0.065 |

In the above Table the cells come from an established cell line and there is no need for a density gradient separation process. In the case of clinical cervix material similar storage methods can be applied either before or after the density gradient separation. This is an important step in the procedure if the test is to be considered for practical application in a busy gynaecology clinic or colposcopy unit.

Gradient Separation

The discontinuous density gradient is obtained by preparing solutions of Percoll (<25 mOs/kg $H_2O$ density of 1.130 g/ml, Pharmacia) of different density and carefully layering these on top of each other avoiding any mixing and in descending order of density.

The formula used to prepare the dilutions is shown below:

$$V_0 = V\frac{P - (0.1 \times P_{10}) - 0.9}{P_O - 1}$$

where $V_0$=volume of Percoll (stock) ml v=volume of final working solution ml

P=desired density of final solution g/ml $P_0$=density of Percoll (stock) g/ml $P_{10}$=density of 1.5M NaCl=1.058 g/ml Therefore for a final working solution (V) of 100 mls and a desired density (P) of 1.085 g/ml and a density of the stock Percoll ($P_0$) of 1.130 g/ml, the amount of stock Percoll to be added is 60.92 mls. The osmolarity is maintained by addition of 10 mls of 1.5M NaCl ($P_{10}$). The final volume of 100 mls is made up with distilled water.

The most suitable densities for the separation of cervical cells have been found to be 1.085 g/ml, 1.055 g/ml, 1.035 g/ml, 1.025 g/ml. These may be altered by omitting one or two of the densities if the contamination in the starting material is minimal. Equally if the starting material has a high concentration of contaminating material then a repeated gradient separation may be necessary. Each solution is carefully layered on top of another.

The cell suspension is shaken of the brush or spatula into the PBS solution. Following gentle syringing using a 1 ml syringe with a 21G×1½" needle to disperse the cells, the whole suspension is centrifuged at 800–1000 rpm (400×g) in a bench top centrifuge for 5 minutes. The supernatant is carefully removed to leave approximately 1 ml of suspension of cells. This is carefully layered onto the previously prepared discontinuous density gradient and centrifuged at 2000 rpm (900×g) for 10 minutes.

This produces several different bands of cells which can be removed into separate tubes. The top layer contains a mixture of bacterial, inflammatory and epithelial cells. The central bands contain predominantly epithelial cells and occasionally some basal cells and these are the cells of interest. There can be up to three of these central bands and they are morphologically indistinguishable from one another. These are usually combined. The bottom layer contains red blood cells, dead cells and cell debris. The cells are washed twice with PBS to remove the Percoll. Refinement of this method includes the further elimination of contaminating white blood cells. This often requires a further separation step, which involves either passing them through the same gradient a second time or using a Ficoll gradient to separate them (centrifugation at 400×g for 10 minutes). In this case the white cells remain on the surface and the epithelial cells will settle to the bottom. The gradient preparation is entirely suitable for automation and several preformed discontinuous gradients can be frozen down and thawed without loss of the buoyant density properties.

EXAMPLE 2

CYTOCHEMICAL DETERMINATION OF 6PGD ACTIVITY IN WHOLE CELLS

An advantage of the cytochemical estimation is the confirmation that the activity of the enzymes of the pentose phosphate shunt being measured, actually derives from the separated cells. In this case the second enzyme in the pathway is measured because there is a longer incubation period involved during which time glucose-6-phosphate could be substantially metabolised by the glycolytic pathway. The cytochemical estimation therefore uses 6-phosphogluconate dehydrogenase as an estimate of the pentose phosphate shunt activity.

The material is obtained as described in Example 1 and similarly passed through a discontinuous Percoll density gradient. After cell selection and washing of the cells a sparse population of these is smeared onto prewashed slides and allowed to air-dry.

In this system the final electron acceptor is NBT instead of DcPIP in the biochemical system. NBT is a yellow coloured complex which, upon reduction forms a blue precipitate. The reaction sequences are:

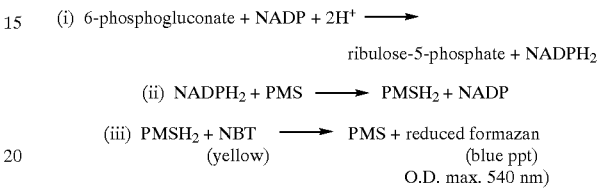

This formazan precipitate has a characteristic absorption maximum at 540 nm and is visible by light microscopy as insoluble particles within the cytoplasm of the cells. The intensity of staining is proportional to the enzyme activity and varies in each individual cell. In the absence of either 6PG or NADP+ no staining occurs. The absorbance at 540 nm is measured using computerised microdensitometry. In brief, the method employs comparison of the digitized image of cells selected by the operator with a blank background field from the same slide and calculates the individual absorbances of the picture elements (pixels) from which the total and mean absorbances can be obtained. The video images are obtained using a Hitachi KP4 video camera mounted in a Zeiss photomicroscope using a narrowband interference filter ($\lambda$=540±10 nm) (Glen Spectra Ltd) and a 10× objective lens. Luminosity data are handled by an Intellect 200 Image Analysing system interfaced to a PDP 11/23+ host computer employing a version of the "CYTABS" (copyright DJS) programme.

Kit Formulation For 100 tests:

| | | |
|---|---|---|
| Percoll reagents, as required | 60 mls of 0.5M aqueous solution (4° C.) | A |
| glycyl glycine buffer (pH 8.5) | | |
| 6-phosphogluconate (6PG.trisodium salt) | 20 mls of 10 mM aqueous frozen vial (−20° C.) | B |
| NADP+ (sodium salt) | 10 mls of 5 mM aqueous frozen vial (−20° C.) | C |
| nitrotetrazolium blue (NBT) | 10 mls of 1% aqueous frozen vial (−20° C.) | D |
| phenazine methosulphate (PMS) | 4.3 mgs frozen vial (−20° C.) | E |

The procedure is as follows:

1. Smear the separated cells onto a clean glass slide and allow to air-dry.

2. Mix A+B+C+D+E+10 mls of distilled water into a light protected vessel.

3. Very carefully add 1 ml per sample onto the slide covering the entire cell smear.

4. Incubate this immediately at 37° C. in the dark for 40 minutes.

5. Gently pour off the reaction mixture, wash very carefully twice with distilled water.

6. Fix in ethanol (1 minute, 70%; 1 minute 90%; 1 minute 95% and 1 minute 100%).

7. Clear in Xylene.

8. Mount in Depex mounting medium.

In normal smears the majority of cells have low absorbance values. In contrast, many of the abnormal smears, i.e. CIN 1, 2 or 3 contain a proportion of cells with significantly higher absorbance values. By taking a particular "cut-off" point of 0.15 optical density units and counting the number of cells with staining intensities greater than this value it is possible to compare results from normal and precancerous samples. Adjustment of the programme to include this as an automated step is readily achievable. An example of some of the material analysed in this way is given below:

TABLE 2

| diagnosis | total no. cells | no. cells with O.D.540 > 0.15 | percentage of total nos. of cells |
|---|---|---|---|
| normal | 119 | 0 | 0 |
| normal | 105 | 0 | 0 |
| normal | 104 | 0 | 0 |
| normal | 116 | 3 | 2.6 |
| normal | 97 | 3 | 3 |
| normal | 127 | 5 | 3.9 |
| normal | 101 | 4 | 4 |
| normal | 124 | 11 | 8.9 |
| normal | 112 | 11 | 9.8 |
| normal | 104 | 19 | 18.3 |
| CIN 1 | 114 | 1 | 0.9 |
| CIN 1 | 105 | 9 | 8.6 |
| CIN 1 | 102 | 13 | 12.7 |
| CIN1 | 107 | 17 | 15.9 |
| CIN 1 | 70 | 11 | 16.0 |
| CIN 1 | 104 | 17 | 16.4 |
| CIN 1 | 102 | 23 | 23.0 |
| CIN 2 | 103 | 6 | 5.8 |
| CIN 2 | 66 | 8 | 12.0 |
| CIN 2 | 105 | 15 | 14.3 |
| CIN 2 | 100 | 12 | 12.0 |
| CIN 2 | 116 | 21 | 18.0 |
| CIN 2 | 111 | 28 | 25.0 |
| CIN 2 | 105 | 30 | 29.0 |
| CIN 2 | 116 | 38 | 33.0 |
| CIN 3 | 10 | 20 | 19.6 |
| CIN 3 | 116 | 23 | 19.8 |
| CIN 3 | 104 | 29 | 27.9 |
| CIN3 | 131 | 41 | 31.3 |
| CIN 3 | 120 | 40 | 33.4 |
| CIN 3 | 101 | 35 | 35.0 |
| CIN 3 | 113 | 41 | 6.3 |
| CIN 3 | 118 | 45 | 38.1 |
| CIN 3 | 112 | 63 | 56.3 |

Expressed as a percentage of the total number of cells measured, this produces a similar distribution to that of the biochemical test (see Example 3). Taking into account that nearly $10^3$×as many cells are measured in the biochemical assay, (see Example 3) the cytochemical results produce a greater overlap between normal and CIN samples. With advancement of the microdensitometry programmes developed for the cytochemical test a larger cell population can be measured in a shorter space of time thus increasing the sensitivity of this method to that of the biochemical test.

EXAMPLE 3

BIOCHEMICAL DETERMINATION OF G6PD ACTIVITY IN LYSED EPITHELIAL CELLS (1) Counting and subsequent lysis of cells The procedure requires small tubes containing 0.4 mls PBS, 50 μl 2% trypan blue and 50 μl cell suspension. The separated cells are counted by haemocytometer, the trypan blue uptake noted, and the number of white cells present is estimated. The cells are centrifuged again and the PBS replaced by 0.5 mls of 0.1% Nonidet P40 detergent to lyse the cells. The cell lysate is vortexed and placed on ice.

(2) Biochemical method

The method employed is based on the first step in the pentose phosphate stunt pathway, which is a salvage pathway of glucose metabolism generating NADPH necessary for biosynthesis of lipids and other reducing reactions as well as ribose-5-phosphate which is an essential precursor for the synthesis of nucleic acids. The pathway is stimulated in cell proliferation due to the increased requirement of DNA synthesis.

The assay uses two substrates (G6P and NADP+), a cycling electron acceptor and a final electron acceptor. The final electron acceptor is a coloured complex, which, upon reduction loses its colour. The rate of disappearance of colour is proportional to the enzyme activity in the sample tested. The two electron acceptors are phenazine methosulphate (PMS) and 2,6-dichlorophenoindophenol (DcPIP) and the reaction is as follows:

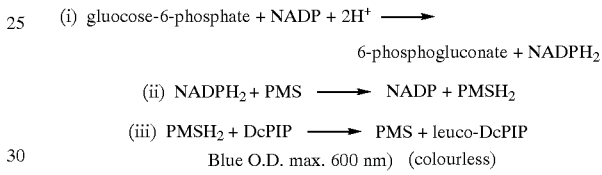

The disappearance of the blue colour is monitored by spectrophotometry at 600 nm. A typical procedure consisting of cell processing and enzyme determination includes cell harvesting, density gradient centrifugation followed by counting the cells, lysing of the cells and spectrophotometric measurement.

Kit Formulation For 20 tests

| Glycyl glycine buffer | 20 mls of 0.5M (ph 8.5), 4° C. | A |
|---|---|---|
| Glucose-6-phosphate (G6P, sodium salt) | 6 mls of 59 mM aqueous frozen vial, −20° C. | B |
| NADP+ (sodium salt) | 5 mls of 10 mM aqueous frozen vial, −20° C. | C |
| Dichlorophenoindophenol (DcPIP) | 2.8 mls of 2 mM aqueous frozen vial, −20° C. (stored in dark vessel). | D |
| Phenazine methosulphate (PMS) | 12 mgs. in a dark vessel | E |
| Nonidet P40 | 100 mls of 0.1% (4° C.) | |
| Glucose-6-phosphate dehydrogenase enzyme standard | 50 mls in 0.1% Nonidet P40 (4° C.) | |

In addition to the above, 4 bottles of prepared Percoll densities (1.085, 1.055, 1.035 and 1.025 g/ml) each of 20 ml are supplied for the cell separation together with instructions as in Example 1.

Instructions to operator Before measuring:

Switch on the spectrophotometer, set the wavelength to 600 nm. Set to fix wavelength and time record. Calibrate recorder. Separate cells on density gradient as described.

Counting of cells

Depending on cell density add either 0.5 mls or 1.0 mls of PBS to the cell pellet. To small tubes add 0.4 mls PBS, 50

μl cell suspension. Count in haemocytometer. Calculate total number of cells taking the dilution factor into account. Spin down the cell suspension. Remove the PBS, add 0.5 mls cold 0.1% Nonidet P40 to each sample and vortex. Place on ice. Take G6PD standard and place on ice.

Prepare reaction mixture

Defrost all ampoules, making sure that DcPIP and PMS are protected from light as these are very light sensitive. Mix A+B+C+D+50 mls distilled water. Protect this mixture from light. Place it on a 25° C. water bath with spectrophotometer. Make up PMS (E) to 4 mls with distilled water. Protect from light.

Measurement

The decrease in intensity of DcPIP is measured at 600 nm. To 2 cuvettes add 2.95 mls reaction mixture. Add 50 μl of PMS(E) to both. Invert to mix. Add 0.5 mls NP40 carefully to one cuvette. Ensure no bubbles are present (invert). Place this into the sample section. Place the other cuvette into the reference section. Add 0.5 mls detergent sample into this cuvette, mix with rounded plastic paddle and immediately autozero and measure rate (decrease in absorbance) for 2 mins.

Standard

Repeat as above, but use detergent diluted G6PD enzyme instead.

Our results using this method have shown that samples from normal smears taken from patients visiting a routine health centre have very low G6PD activity compared to cases of CIN. All the cases of CIN were diagnosed by conventional histology. The data below illustrates the potential of this method to produce the minimum number of false positives and false negatives, although it does not distinguish between grades of CIN.

TABLE 3

G6PD activity (units/min per $10^4$ cells × $10^{-5}$)

| Normal | CIN 1 | CIN 2 | CIN 3 | invasive carcinoma |
|--------|-------|-------|-------|--------------------|
| 0      | 0     | 19    | 180   | 6000               |
| 0      | 20    | 30    | 230   | 10,000             |
| 0      | 45    | 46    | 430   |                    |
| 0      | 53    | 59    | 530   |                    |
| 0      | 74    | 67    | 550   |                    |
| 0      | 181   | 110   | 600   |                    |
| 0      | 250   | 310   | 605   |                    |
| 0      | 328   | 340   | 620   |                    |
| 1.4    | 820   | 450   | 803   |                    |
| 2.0    |       | 890   | 917   |                    |
| 2.0    |       |       | 946   |                    |
| 3.0    |       |       | 2940  |                    |
| 8.9    |       |       |       |                    |
| 6.0    |       |       |       |                    |
| 7.0    |       |       |       |                    |
| 9.7    |       |       |       |                    |
| 27.0   |       |       |       |                    |
| 36.0   |       |       |       |                    |
| 38.0   |       |       |       |                    |

For this combined measurement the operator requires the kit formulation given for measurement of G6PD and also a solution of 0.1M hydrogen peroxide, an oxygen electrode, a water bath at 37° C. and a chart recorder. If the chamber of the oxygen electrode takes a volume of 1.9 mls the cell lysate will occupy 1.5 mls. 200 μl of peroxide (0.1M) are then added and the rate followed after calibration of the monitor and chart recorder.

Assuming that the activities measured are related to the amount of enzyme present, measurement of the amount of G6PD present in cells instead of activity, is possible by the use of a fluorescent antibody to human G6PD which can be estimated by flow cytometry. This has the advantage of very rapid assessment, single cell analysis and the possible omission of the cell separation, because of the facility of flow cytometry to be able to discriminate between cell populations.

EXAMPLE 4

ENZYME RATIO METHOD—G6PG/CATALASE

Modification of the assays described in the previous Examples includes the simultaneous measurement of a second parameter which is decreased in malignant cells. Enzymes such as xanthine oxidase and catalase are easily measured and detection of abnormality can be improved by expression of increased enzyme and decreased enzyme activities as a ratio. As an example the simultaneous measurement of catalase in separated cells is described.

The cells are processed as described above for the biochemical assay, i.e. gradient separation, cell counting and lysis. The sample is divided and one half of the lysate is used for G6PD determination, the other half of the lysate is used to determine catalase activity. Catalase readily decomposes hydrogen peroxide to oxygen and water:

$$2H_2O_2 \longrightarrow 2H_2O + O_2$$

The oxygen produced can be readily monitored by an oxygen electrode. The amount of oxygen produced is expressed as % $O_2$ production per minute per $10^4$ cells×$10^{-5}$. Therefore the ratio of e.g. G6PD catalase activity can be expressed as:

$$\frac{\text{Rate } (G6P)/\min/10^4 \text{ cells} \times 10^5}{\text{Rate (catalase)}/\min/10^4 \text{ cells} \times 10^{-5}} = \frac{G6PD \text{ activity}}{\text{catalase activity}}$$

Some examples of catalase and simultaneous G6PD estimations are given below:

TABLE 4

| diagnosis | catalase % $O_2$/min/$10^4$cells $10^{-5}$ | G6PD u/min/$10^4$cells $10^{-5}$ | Ratio G6PD/catalase |
|-----------|--------------------------------------------|-----------------------------------|---------------------|
| normal    | 17    | 0    | 0     |
| normal    | 56    | 0    | 0     |
| normal    | 27    | 0    | 0     |
| normal    | 30    | 0    | 0     |
| normal    | 32    | 0    | 0     |
| normal    | 39    | 0    | 0     |
| normal    | 59    | 0    | 0     |
| normal    | 98    | 0    | 0     |
| normal    | 100   | 0    | 0     |
| normal    | 233   | 0    | 0     |
| normal    | 435   | 0    | 0     |
| normal    | 539   | 0    | 0     |
| CIN 1     | 36    | 0    | 0     |
| CIN 1     | 23    | 139  | 6.4   |
| CIN 1     | 36    | 453  | 12.6  |
| CIN 1     | 9     | 471  | 52.3  |
| CIN 2     | 62    | 90   | 1.5   |
| CIN 2     | 11    | 2.3  | 2.1   |
| CIN 2     | 73    | 2023 | 28.0  |
| CIN 2     | 6     | 400  | 67.0  |
| CIN 2     | 0.44  | 163  | 370.0 |
| CIN 3     | 33    | 238  | 7.2   |

TABLE 4-continued

| diagnosis | catalase<br>% O$_2$/min/10$^4$cells<br>10$^{-5}$ | G6PD<br>u/min/10$^4$cells<br>10$^{-5}$ | Ratio<br>G6PD/catalase |
|---|---|---|---|
| CIN 3 | 36 | 458 | 13.0 |
| CIN 3 | 33 | 440 | 13.3 |
| CIN 3 | 19 | 435 | 23.0 |
| CIN 3 | 9.3 | 500 | 54.0 |
| CIN 3 | 4.7 | 284 | 60.0 |

We claim:

1. A method of testing for a malignant or pre-malignant condition of the cervix by examination of a cervical smear, which comprises
   fractionating cells in said cervical smear to obtain a cell fraction consisting predominantly of squamous epithelial cells, and
   subjecting said cell faction to a quantitative examination of characteristics indicative of said malignant or premalignant condition.

2. The method according to claim 1, in which the squamous epithelial cells are fractionated by means of antibodies which bind said squamous epithelial cells.

3. The method according to claim 1, in which the test is performed on intact cells.

4. The method according to claim 3, wherein said examining step is conducted using flow-cytometry.

5. The method according to claim 3, which comprises the quantitative estimation of a marker formed in, or taken up by, the cells.

6. The method according to claim 5, in which the estimation is by means of a cell-staining method.

7. The method according to claim 1, in which the squamous epithelial cells are fractionated by a buoyant density method.

8. The method according to claim 7, in which the fractionation is effected by density gradient centrifugation.

9. The method according to claim 8, in which a discontinuous gradient is used.

10. The method according to claim 8, in which the cell fraction is, or corresponds to, the fraction of density range from about 1.035 to about 1.055 g/ml as measured in a Percoll density gradient.

11. The method according to claim 8, wherein the fractionated cells are further purified by gradient centrifugation.

12. The method according to claim 8, wherein further purification is carried out on a Percoll or Ficoll gradient.

13. The reagent kit according to claim 8, comprising gradient material for use in the centrifugal separation of squamous epithelial cells from the cell sample.

14. The reagent kit according to claim 13, comprising separate solutions of gradient materials to provide a suitable density range for a discontinuous gradient, or dry materials for reconstitution as such solutions.

15. The reagent kit according to claim 14, comprising materials for a Percoll gradient over the density range 1.035 to 1.055 g/ml or other gradient materials equivalent thereto.

16. The method according to claim 1, in which the test is performed on lysed cells.

17. The method according to claim 16, in which the test is for an abnormal level of an enzyme associated with proliferating cells.

18. The method according to claim 17, in which the enzyme tested for is one selected from the group consisting of pentose phosphate shunt enzymes, ornithine decarboxylase, thymidine kinase, and ribonucleotide reductase.

19. The method according to claim 17, in which the enzyme tested for is glucose-6-phosphate dehydrogenase.

20. The method according to claim 17, in which an electron coupling system is used to increase the sensitivity of the test.

21. The method according to claim 17, in which a method of quantitative measurement is used.

22. The method according to claim 17, in which the enzyme tested for is 6-phosphogluconate dehydrogenase.

23. The method according to claim 17, which comprises also measuring the level of an enzyme which is repressed in the condition tested for and determining the ratio of the levels of the two respective enzymes.

24. The method according to claim 23, in which the repressed enzyme is catalase or xanthine oxidase.

25. A method of testing for a malignant or pre-malignant condition of the cervix by examination of a cervical smear, which comprises
   fractionating cells in said cervical smear to obtain a cell fraction consisting predominantly of squamous epithelial cells; and
   subjecting said cell fraction to a cytochemical or biochemical reaction of the cells or cell components; thereby providing a quantitative indication of the presence of said condition.

26. The method according to claim 25, in which the squamous epithelial cells are separated from the sample.

27. The method according to claim 26, which comprises subjecting the sample to discontinuous gradient centrifugation, harvesting cells corresponding to combined fractions of cells having densities within the range 1.035 to 1.055 g/ml as measured in a Percoll gradient, counting and then lysing the harvested cells, determining the amounts in the lysate of two enzymes, one of which is enhanced and the other repressed in the condition under test, and calculating the ratio of the amounts of the two enzymes.

28. The method according to claim 26, wherein in said subjecting step the separated cells are counted and then lysed and the lysate is subjected to quantitative estimation of at least one enzyme which is present in above-normal levels of activity or amount, in proliferating cells.

29. The method according to claim 28, in which the enzyme is an enzyme of the pentose phosphate shunt.

30. The method according to claim 29, in which the enzyme is glucose-6-phosphate-dehydrogenase.

31. The method according to claim 29, in which the enzyme is 6-phosphogluconate dehydrogenase.

32. A reagent kit for use in the detection of a pre-malignant or malignant condition of the cervix by testing of squamous epithelial cells derived from a cervical cell sample, said kit comprising a reagent material for fractionating squamous epithelial cells from said cervical cell sample, a substrate for an enzyme which is present at an increased level in the condition tested for, a cycling electron acceptor for the enzyme, and a final electron acceptor which upon reduction provides a measurable indication which correlates with the level of said enzyme present in said cervical sample.

33. The reagent kit according to claim 32, in which the reagent material for separating squamous epithelial cells comprises antibodies selective for said squamous epithelial cells.

34. The reagent kit according to claim 32, further comprising a reagent for lysing the squamous epithelial cells.

35. The reagent kit according to claim 32, in which the cycling electron acceptor is phenazine methosulphate.

36. The reagent kit according to claim 32, in which the final electron acceptor is 2,6-dichlorophenoindophenol or nitroblue-tetrazolium.

37. The reagent kit according to claim 32, further comprising one or more reagents for estimating the level of an enzyme which is repressed in the condition tested for.

38. The reagent kit according to claim 37, in which the repressed enzyme is catalase.

39. The reagent kit according to claim 32, in which the enzyme is selected from the group consisting of pentose phosphate shunt enzymes, ornithine decarboxylase, thymidine kinase, and ribonucleotide reductase.

40. The reagent kit according to claim 39, in which the enzyme is 6-phosphogluconate dehydrogenase.

41. The reagent kit according to claim 39, in which the enzyme is glucose-6-phosphate dehydrogenase.

42. The reagent kit according to claim 41, wherein said substrate concentrations are within the ranges of 2.5 and 3.5 Mm glucose-6-phosphate; 0.45 and 0.55 Mm NADP$^+$; 0.055 and 0.065 Mm DcPIP or NBT; 0.10 and 0.18 Nm PMS for both the cytochemical and biochemical assay.

* * * * *

UNITED STATES PATENT AND TRADEMARK OFFICE
CERTIFICATE OF CORRECTION

| | |
|---|---|
| PATENT NO. : 6,051,393 | Page 1 of 1 |
| DATED : April 18, 2000 | |
| INVENTOR(S) : Jonas et al. | |

It is certified that error appears in the above-identified patent and that said Letters Patent is hereby corrected as shown below:

<u>Title page,</u>
Items [19] and [76], delete "Jones" and replace -- Jonas -- (both occurrences)

Following Item [63], insert new paragraph

-- [30] Foreign Application Priority Data
Sept 25, 1992 [WO] WIPO PCT/GB92/01768
Sept 27, 1991 [GB] Great Britain 9120633.4 --

<u>Claim 13,</u>
Line 1, delete "8" and replace by -- 32 --

Signed and Sealed this

Sixteenth Day of April, 2002

Attest:

JAMES E. ROGAN
*Attesting Officer*     *Director of the United States Patent and Trademark Office*